United States Patent
Levanony et al.

(10) Patent No.: US 11,526,700 B2
(45) Date of Patent: Dec. 13, 2022

(54) ANNOTATING UNLABELED DATA USING CLASSIFIER ERROR RATES

(71) Applicant: International Business Machines Corporation, Armonk, NY (US)

(72) Inventors: Dana Levanony, Tel Aviv (IL); Efrat Hexter, Beit Shemesh (IL)

(73) Assignee: International Business Machines Corporation, Armonk, NY (US)

( * ) Notice: Subject to any disclaimer, the term of this patent is extended or adjusted under 35 U.S.C. 154(b) by 277 days.

(21) Appl. No.: 16/915,516

(22) Filed: Jun. 29, 2020

(65) Prior Publication Data

US 2021/0406608 A1  Dec. 30, 2021

(51) Int. Cl.
| | | |
|---|---|---|
| *G06K 9/62* | (2022.01) | |
| *G16H 30/40* | (2018.01) | |
| *G06F 17/16* | (2006.01) | |
| *G06N 3/08* | (2006.01) | |
| *G06N 5/04* | (2006.01) | |

(52) U.S. Cl.
CPC .......... *G06K 9/6262* (2013.01); *G06F 17/16* (2013.01); *G06K 9/6259* (2013.01); *G06K 9/6261* (2013.01); *G06K 9/6268* (2013.01); *G06N 3/084* (2013.01); *G06N 5/046* (2013.01); *G16H 30/40* (2018.01)

(58) Field of Classification Search
CPC .. G06K 9/6262; G06K 9/6259; G06K 9/6261; G06K 9/6268; G06F 17/16; G06N 3/084; G06N 5/046; G16H 30/40; G16H 50/20; G16H 50/70
USPC ....................................................... 702/182
See application file for complete search history.

(56) References Cited

U.S. PATENT DOCUMENTS

| | | | | |
|---|---|---|---|---|
| 7,426,497 B2 * | 9/2008 | Bacioiu | ................. | G06N 20/00 706/20 |
| 7,672,915 B2 * | 3/2010 | Dara | ................... | G06K 9/6256 706/20 |
| 8,014,591 B2 * | 9/2011 | Baker | ................. | G06K 9/6256 700/47 |
| 9,477,906 B2 | 10/2016 | Röder et al. | | |
| 2018/0150728 A1 | 5/2018 | Vahdat | | |
| 2019/0164086 A1 | 5/2019 | Amit et al. | | |
| 2019/0244138 A1 | 8/2019 | Bhowmick et al. | | |

(Continued)

FOREIGN PATENT DOCUMENTS

| | | |
|---|---|---|
| CN | 107909143 A | 4/2018 |
| CN | 110447039 A | 11/2019 |

(Continued)

OTHER PUBLICATIONS

Iscen, Ahmet et al., "Label Propagation for Deep Semi-supervised Learning," 2019 IEEE/CVF Conference on Computer Vision and Pattern Recognition (CVPR), Jun. 15, 2019, 10 pages.

(Continued)

*Primary Examiner* — Juan A Torres
(74) *Attorney, Agent, or Firm* — Barry D. Blount

(57) ABSTRACT

An example system includes a processor to evaluate a trained first classifier on a test set of labeled data to generate error rates for a number of labels. The processor is to process a set of unlabeled data via the trained first classifier to generate annotated data including labels and associated error rates. The processor is to train a second classifier using the annotated data and the associated error rates.

25 Claims, 8 Drawing Sheets

(56) References Cited

U.S. PATENT DOCUMENTS

2019/0354857 A1 11/2019 Sallee et al.
2021/0142168 A1* 5/2021 Kushnir ................ G06N 3/063

FOREIGN PATENT DOCUMENTS

CN 110503127 A 11/2019
CN 111310860 A 6/2020

OTHER PUBLICATIONS

Liu, Xiuming et al., "Robust Semi-Supervised Learning when Labels are Missing at Random," Uppsala University, Dept. Information Technology, Nov. 27, 2018, 6 pages.
Palotai, Zsolt et al., "LabelMovie: Semi-supervised machine annotation tool with quality assurance and crowd-sourcing options for videos," 2014 12th International Workshop on Content-Based Multimedia Indexing (CBMI), Jun. 18, 2014, 5 pages.
Patrini, Giorgio et al., "Making Deep Neural Networks Robust to Label Noise: a Loss Correction Approach," Mar. 22, 2017, 9 pages.
"International Search Report and Written Opinion of the International Searching Authority", dated Aug. 24, 2021, International Application No. PCT/IB2021/054038, 8 pages.

* cited by examiner

200B

300

ANNOTATING UNLABELED DATA USING CLASSIFIER ERROR RATES

BACKGROUND

The present techniques relate to training classifiers. More specifically, the techniques relate to training classifiers using automatically annotated data.

Classifiers may be trained using labeled data. For example, such labeled data may be annotated by a human. As one example, a human annotator may manually label a set of images. Semi-supervised methods of annotating are also used to label data. However, these semi-supervised methods may rely on either joint training with a supervised network, or may use similarity and clustering to identify closely related data points. Such semi-supervised methods may provide much lower performance than supervised methods. In addition, in the context of medical imaging, the annotation may be performed by experts such as physicians, which may add extra burdens to the costs of annotation.

SUMMARY

According to an embodiment described herein, a system can include processor to evaluate a trained first classifier on a test set of labeled data to generate error rates for a plurality of labels. The processor can also further process a set of unlabeled data via the trained first classifier to generate annotated data including labels and associated error rates. An advantage of using unlabeled data is that such data does not need to be manually labeled or annotated. The processor can also train a second classifier using the annotated data and the associated error rates. Preferably, the processor can compute a flipped labels probability matrix based on the associated error rates. Preferably, the trained classifier is trained to classify a training set of the labeled data. Optionally, the processor is to train the second classifier using a forward corrected loss. An advantage of using a forward corrected loss is noise robustness. Optionally, the processor is to train the second classifier using a backward corrected loss. An advantage of using a backward corrected loss is that the backward corrected loss is differentiable and can be minimized with any suitable back-propagation algorithm.

According to another embodiment described herein, a computer-implemented method can include evaluating, via a processor, a trained first classifier on a test set of labeled data to generate error rates for a plurality of labels. The method can further include generating, via the trained first classifier, annotated data including labels and associated error rates based on a set of unlabeled data. An advantage of using unlabeled data is that such data does not need to be manually labeled or annotated. The method can also further include training, via the processor, a second classifier using the annotated data and the associated error rates. Preferably, training the second classifier includes computing a flipped labels probability matrix based on the error rates and calculating a loss based on the flipped labels probability matrix. Preferably, the method can include receiving the labeled data, splitting the labeled data into the test set and a training set, and training the first classifier to classify the training set of the labeled data. Optionally, training the second classifier includes using a forward corrected loss. An advantage of using a forward corrected loss is noise robustness. Optionally, training the second classifier includes using a backward corrected loss. An advantage of using a backward corrected loss is that the backward corrected loss is differentiable and can be minimized with any suitable back-propagation algorithm.

According to another embodiment described herein, a computer program product for annotating training data can include computer-readable storage medium having program code embodied therewith. The computer readable storage medium is not a transitory signal per se. The program code executable by a processor to cause the processor to evaluate a trained first classifier on a test set of labeled data to generate error rates for a plurality of labels. The program code can also cause the processor to process a set of unlabeled data to generate annotated data including labels and associated error rates. An advantage of using unlabeled data is that such data does not need to be manually labeled or annotated. The program code can also cause the processor to train second classifier using the annotated data and the associated error rates. Preferably, the program code can also cause the processor to compute a flipped labels probability matrix based on the error rates and calculate a loss based on the flipped labels probability matrix. Preferably, the program code can also cause the processor to receive the labeled data, split the labeled data into the test set and a training set, and train the first classifier to classify the training set of the labeled data. Optionally, the program code can also cause the processor to train the second classifier using a forward corrected loss. An advantage of using a forward corrected loss is noise robustness. Optionally, the program code can also cause the processor to train the second classifier using a backward corrected loss. An advantage of using a backward corrected loss is that the backward corrected loss is differentiable and can be minimized with any suitable back-propagation algorithm.

According to another embodiment described herein, a system can include a processor to receive data to be classified. The processor can also classify the set of data via a classifier trained on annotated data generated from unlabeled data by a second classifier, wherein the classifier is trained using a loss based on error rates generated by the second classifier. An advantage of using unlabeled data is that such data does not need to be manually labeled or annotated. Preferably, the loss is based on a flipped labels probability matrix computed based on the error rates. Optionally, the loss includes a forward corrected loss. Optionally, the loss includes a backward corrected loss. In some examples, the data may include a medical image.

According to another embodiment described herein, a computer-implemented method includes receiving, via a processor, data to be classified. The method can further include classifying, via a classifier trained on annotated data generated from unlabeled data by a second classifier, the set of data, wherein the classifier is trained using a loss based on error rates generated by the second classifier. An advantage of using unlabeled data is that such data does not need to be manually labeled or annotated. An advantage of using a loss correction is that it is integrated into the training and can be mathematically proven to be equivalent to training with clean labels. Preferably, the loss is calculated based on a flipped labels probability matrix generated based on the error rates. Optionally, the loss includes a forward corrected loss. An advantage of using a forward corrected loss is noise robustness. Optionally, the loss includes a backward corrected loss. An advantage of using a backward corrected loss is that the backward corrected loss is differentiable and can be minimized with any suitable back-propagation algorithm. In some examples, the data may include a medical image.

DETAILED DESCRIPTION

According to embodiments of the present disclosure, system includes a processor that can evaluate a trained first classifier on a test set of labeled data to generate error rates for a number of labels. The processor can also process a set of unlabeled data via the trained first classifier to generate annotated data including labels and associated error rates. The processor can then train a second classifier using the annotated data and the associated error rates. Thus, embodiments of the present disclosure allow unlabeled data to be used to train a classifier. An advantage of using unlabeled data is that such data does not need to be manually labeled or annotated.

Figure 1:
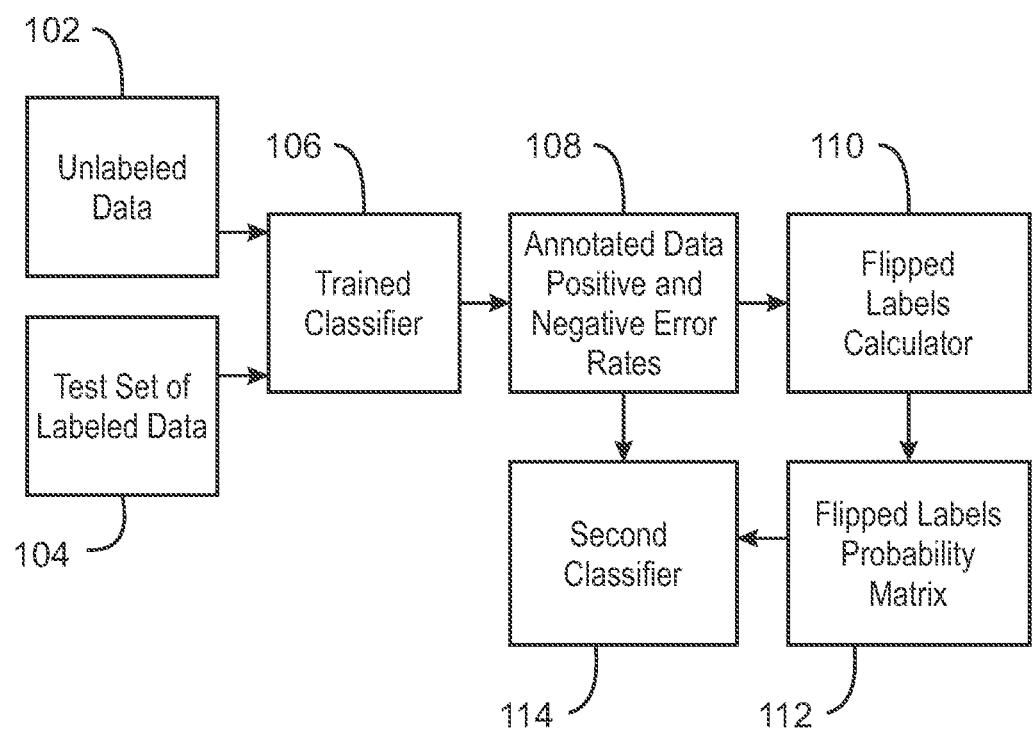
FIG. 1 is a block diagram of an example system for training a classifier using unlabeled data.

With reference now to FIG. 1, a block diagram shows an example system for training a classifier using unlabeled data. The example system 100 may be implemented using the computing device 400 or the computer readable medium 700 of FIGS. 4 and 7, and can be implemented using the method 200A of FIG. 2A or the method 200B of FIG. 2B. FIG. 1 includes unlabeled data 102 and test set 104 of labeled data shown being received at a trained classifier 106. For example, the trained classifier may be a neural network. In various examples, the unlabeled data 102 and the labeled data may be from a similar source. For example, the source may be a collection of medical images of patients. In some examples, the unlabeled data 102 may be unlabeled images of tumorous growths. The labeled data may be labeled images of benign or cancerous tumors. In various examples, the trained classifier 106 may be a neural network trained using a training set of the labeled data. The trained classifier 106 is shown generated annotated data 108 with positive and negative error rates. The system 100 includes a flipped labels calculator 110 communicatively coupled to the trained classifier 106. The flipped labels calculator 110 is shown generating a flipped labels probability matrix. The system 100 further includes a second classifier 114 communicatively coupled to the trained classifier 106 and the flipped labels calculator 110. For example, the second classifier 114 is shown being trained on the annotated data 108 using the flipped labels probability matrix 112.

In the example of FIG. 1, a trained classifier 106 may be used to generate annotated data 108 including labels and associated positive and negative error rates for each of the labels. For example, labeled data may be split into subsets including a training set (not shown) and a test set 104. The trained classifier 106 may be trained using the training set to annotate unlabeled data. The trained classifier 106 may then be used to generate positive and negative error rates for each of a number of labels based on the test set 104. For example, using the labels of the test set 104, an evaluator (not shown) may compute the negative error rate indicating the probability of a label being flipped into not being labeled under noise, and a positive error rate indicating the probability of an object not labeled being labeled under noise. An asymmetric, class-conditional noise setting may be assumed. For example, each label y in the training set may be flipped to $\tilde{y} \in Y$ with probability $p(\tilde{y}|y)$ with feature vectors of a trained neural network untouched. Thus, the negative error rate and positive error rate may have a sum of one. As one example, if the label being evaluated is a cancerous tumor, then the positive error rate would indicate the rate at which tumors are incorrectly flipped by a neural network as cancerous tumors under noise. The negative error rate is the rate at which cancerous tumors are incorrectly flipped as unlabeled under noise. The trained classifier 106 can then generate annotated data 108 based on the unlabeled data. The annotated data 108 may thus include labels associated with the positive and negative error rates generated using the test set.

The flipped labels calculator 110 receives the annotated data 108 with associated positive and negative error rates and generates a flipped labels probability matrix 112 for the labels based on the positive and negative error rates. For example, the error rates can be used as a probability that an image has flipped labels. In various examples, given a known probability of each class to have flipped labels, the flipped labels probability matrix 112 may be a noise transition matrix $T \in [0,1]^{cxc}$ specifying the probability of one label flipped to another, such that $\forall_{i}, j\ T_{ij}=p(\tilde{y}=e^j|y=e^i)$. In various examples, the flipped labels probability matrix 112 may be row-stochastic and not necessarily symmetric across classes. As one example, given a positive error rate of 0.8 and a negative error rate of 0.2 for a particular label, the first row of a flipped labels probability matrix 112 may be 0.8 and 0.2, and the second row may be 0.2 and 0.8.

The second classifier 114 is then trained using a loss based on the flipped labeled probability matrix 112 and the annotated data 108. The second classifier 114 may be trained to classify input annotated data 108 by treating labels as flipped according to the flipped labeled probability matrix 112. The second classifier 114 may be trained using a method that reverts the flipped labels to train such that the second classifier 114 outputs classifications as if the labels were not flipped. For example, the flipped labels may be reverted using a forward corrected loss or a backward corrected loss.

Still referring to FIG. 1, a forward corrected loss may be used to correct model predictions of the trained classifier 106. For example, the forward corrected loss may compare a noisy label $\tilde{y}$ to averaged noisy prediction corrupted by flipped labeled probability matrix T 112. In various examples, the loss used to correct model predictions of the trained classifier 106 may be a proper composite loss. For example, a composite loss can be expressed by the aid of a link function, and a proper composite loss includes a minimizer that assumes a particular shape of the link function applied to the class-conditional probabilities $p(y|x)$. Given a proper composite loss $\ell$, a forward correction loss $\ell_\psi^\rightarrow$ may be defined by the Equation:

$$\ell_\psi^\rightarrow(h(x)) = \ell(T^T\psi^{-1}h(x)) \quad \text{Eq. 1}$$

where $T^T$ is the transpose of flipped labeled probability matrix T, $\psi^{-1}$ is the inverse of link function $\psi$, and h(x) is a transformation function representing the transformations of the intermediate layers of a neural network.

In various examples, a backward corrected loss may be implemented as an unbiased estimator of the loss function, such that under expected label noise the corrected loss equals the original one computed on clean data. For example, given a loss $\ell$ and a non-singular noise matrix T, a backward corrected loss $\ell^\leftarrow$ may be computed using the Equation:

$$\ell^\leftarrow(\hat{p}(y|x)) = T^{-1}\ell(\hat{p}(y|x)) \quad \text{Eq. 2}$$

where $\hat{p}(y|x)$ is the predictor for noisy labels. For example, the predictor may be a neural network trained without any loss correction.

It is to be understood that the block diagram of FIG. 1 is not intended to indicate that the system 100 is to include all of the components shown in FIG. 1. Rather, the system 100 can include fewer or additional components not illustrated in FIG. 1 (e.g., additional data, classifiers, or additional matrices, etc.).

Figure 2A:
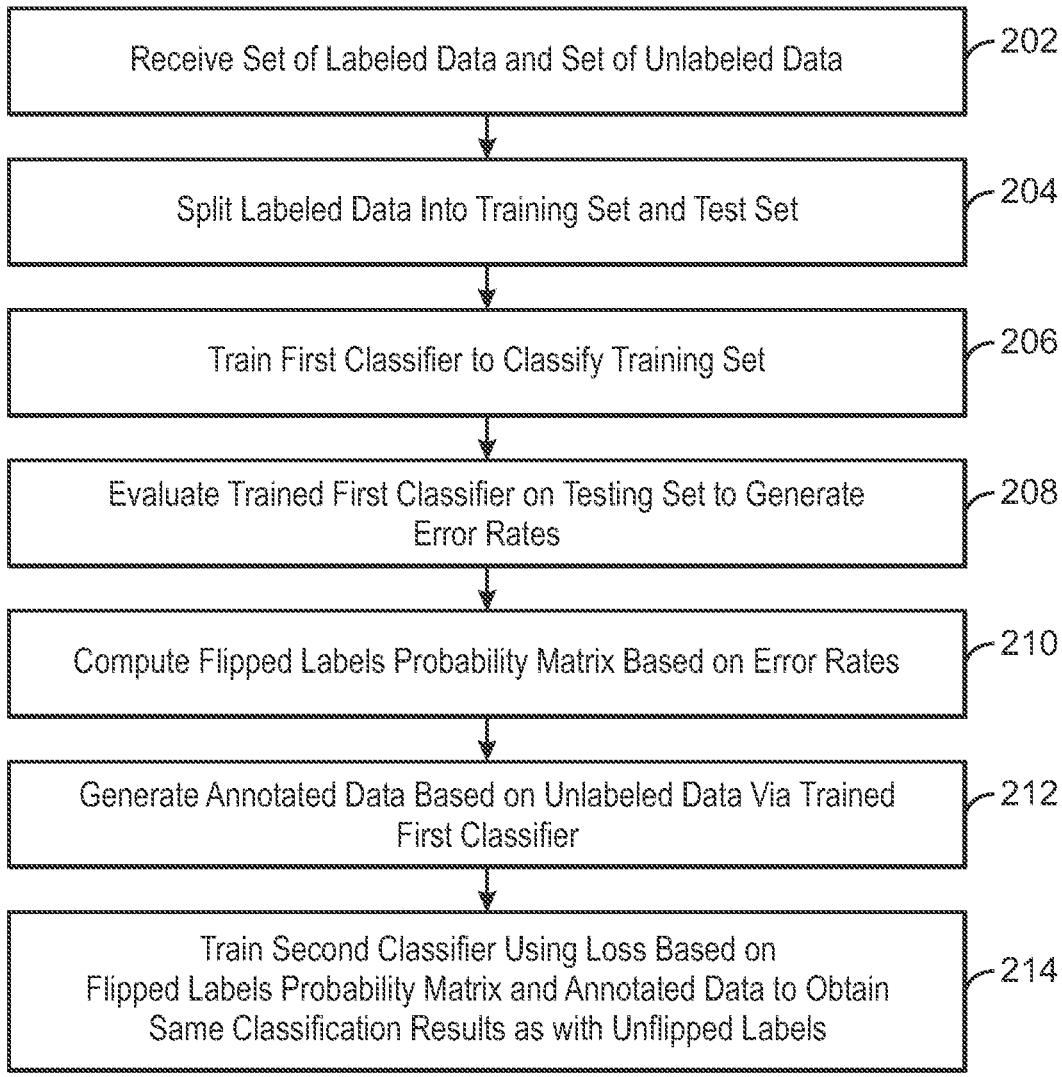
FIG. 2A is a block diagram of an example method that can train a classifier using unlabeled data.

FIG. 2A is a process flow diagram of an example method that can train a classifier using unlabeled data. The method 200A can be implemented with any suitable computing device, such as the computing device 400 of FIG. 4 and is described with reference to the system 100 of FIG. 1. For example, the method 200A can be implemented by the processor 402 or the processor 702 of FIGS. 4 and 7.

At block 202, a set of labeled data and a set of unlabeled data is received. For example, the set of labeled data may include labels for one or more classes. The unlabeled data may not include any labeling. In various examples, the labeled data and the unlabeled data may be from the same data source and thus the same distribution of data. As one example, the data source may be a repository of medical images. The labels may include one or more types of tumors.

At block 204, the labeled data is split into a training set and a test set. For example, the labeled data may be randomly sampled to generate the training set and the test set. In various examples, the size of the training set and a test set may be based on the size of the labeled data set.

At block 206, the first classifier is trained to classify the training set. For example, the first classifier is trained to label input data with any suitable loss function based on the ground truth labels found in the training set. As one example, the loss function may be a cross-entropy loss function. As another example, the loss function used to train the first classifier may be a mean squared error (MSE).

At block 208, the trained first classifier is evaluated on the testing set to generate error rates. For example, a positive error rate and a negative error rate may be generated based on the output labels as compared to the ground truth labels of the testing set.

At block 210, a flipped labels probability matrix is computed based on the error rates. For example, the location(i,j) of the flipped labels probability matrix may be the probability of an image with real label I, to be flopped to label j. This probability may be set by the error matrix produced by the error rates.

At block 212, annotated data is generated via the trained first classifier based on the set of unlabeled data. For example, the trained first classifier may receive the set of unlabeled data and generate a set of annotated data including labels.

At block 214, a second classifier is trained using a loss based on the flipped labels probability matrix and the annotated data to obtain a same classification results as with unflipped labels. For example, the loss function may be a forward correct loss function or a backward corrected loss function computed using the flipped labels probability matrix. Thus, the second classifier may be trained on unlabeled data annotated using the first classifier using a loss function based on error rates associated with the annotated data. In this manner, the second loss function may be trained on any amount of unlabeled data automatically annotated using the first classifier.

The process flow diagram of FIG. 2A is not intended to indicate that the operations of the method 200A are to be executed in any particular order, or that all of the operations of the method 200A are to be included in every case. Additionally, the method 200A can include any suitable number of additional operations.

Figure 2B:
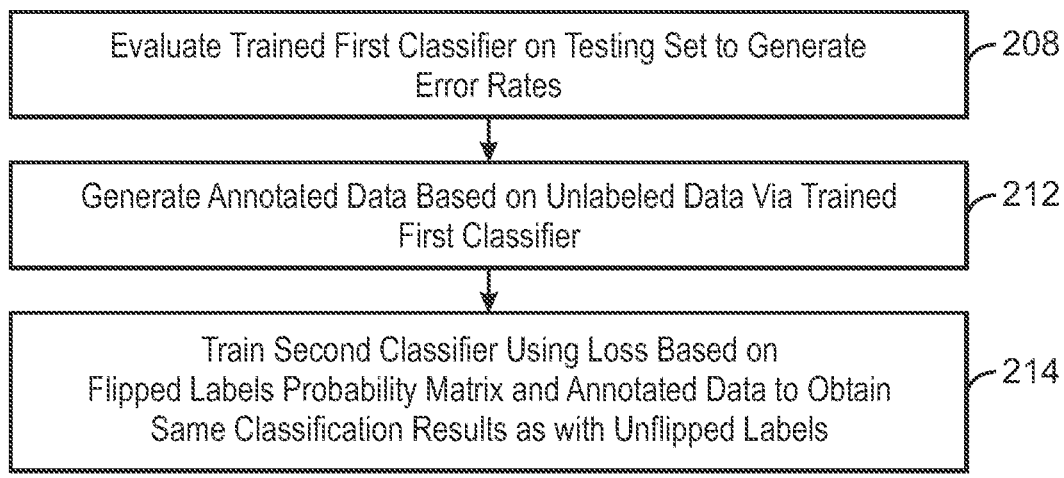
FIG. 2B is a block diagram of another example method that can train a classifier using unlabeled data.

FIG. 2B is a process flow diagram of another example method that can train a classifier using unlabeled data. The method 200B can be implemented with any suitable computing device, such as the computing device 400 of FIG. 4 and is described with reference to the system 100 of FIG. 1. For example, the method 200B can be implemented by the processor 402 or the processor 702 of FIGS. 4 and 7.

The method 200B includes similarly numbered blocks described in FIG. 2A. For example, at block 208 a trained first classifier is evaluated on a testing set to generate error rates. The error rates may include positive and negative rates for each of a number of labels. In various example, the first classifier may be trained based on a training set of labeled data as described in FIG. 2A.

At block 212, annotated data is generated based on unlabeled data via the trained first classifier. For example, the unlabeled data may be from a similar source of data as the training set and the testing set.

At block 214, a second classifier is trained using a loss based on a flipped labels probability matrix and the annotated data to obtain classification results that are the same as being trained with unflipped labels.

The process flow diagram of FIG. 2 is not intended to indicate that the operations of the method 200B are to be executed in any particular order, or that all of the operations of the method 200B are to be included in every case. Additionally, the method 200B can include any suitable number of additional operations. For example, the method 200B can include one or more of the additional blocks shown in method 200A.

Figure 3:
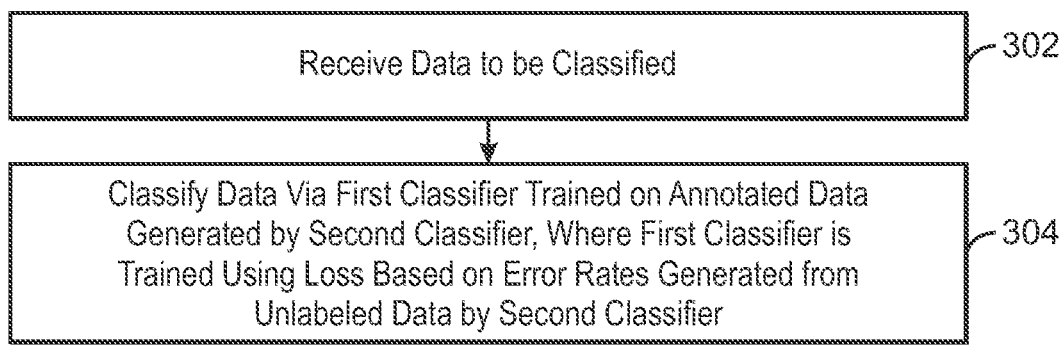
FIG. 3 is a block diagram of an example method that can classify data using a classifier trained on unlabeled data annotated by a second classifier.

FIG. 3 is a process flow diagram of an example method that can classify data using a classifier trained on unlabeled data annotated by a second classifier. The method 300 can be implemented with any suitable computing device, such as the computing device 400 of FIG. 4 and is described with reference to the systems 100 of FIG. 1. For example, the method 300 can be implemented by the processor 402 or the processor 702 of FIGS. 4 and 7.

At block 302, data to be classified is received. For example, the data may be medical images to be classified.

At block 304, a first classifier is trained based on annotated data generated from unlabeled data by a second classifier. For example, the first classifier may be trained using a loss based on error rates generated by the second classifier. In various examples, the annotated data may also be generated by the second classifier based on unlabeled data. In some examples, the loss is based on a flipped labels probability matrix computed based on the error rates. For example, the loss may be a forward corrected loss or a backward corrected loss.

The process flow diagram of FIG. 3 is not intended to indicate that the operations of the method 300 are to be executed in any particular order, or that all of the operations of the method 300 are to be included in every case. Additionally, the method 300 can include any suitable number of additional operations.

In some scenarios, the techniques described herein may be implemented in a cloud computing environment. As discussed in more detail below in reference to at least FIGS. 4-7, a computing device configured to classify data using a classifier trained on unlabeled data annotated by a second classifier may be implemented in a cloud computing environment. It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
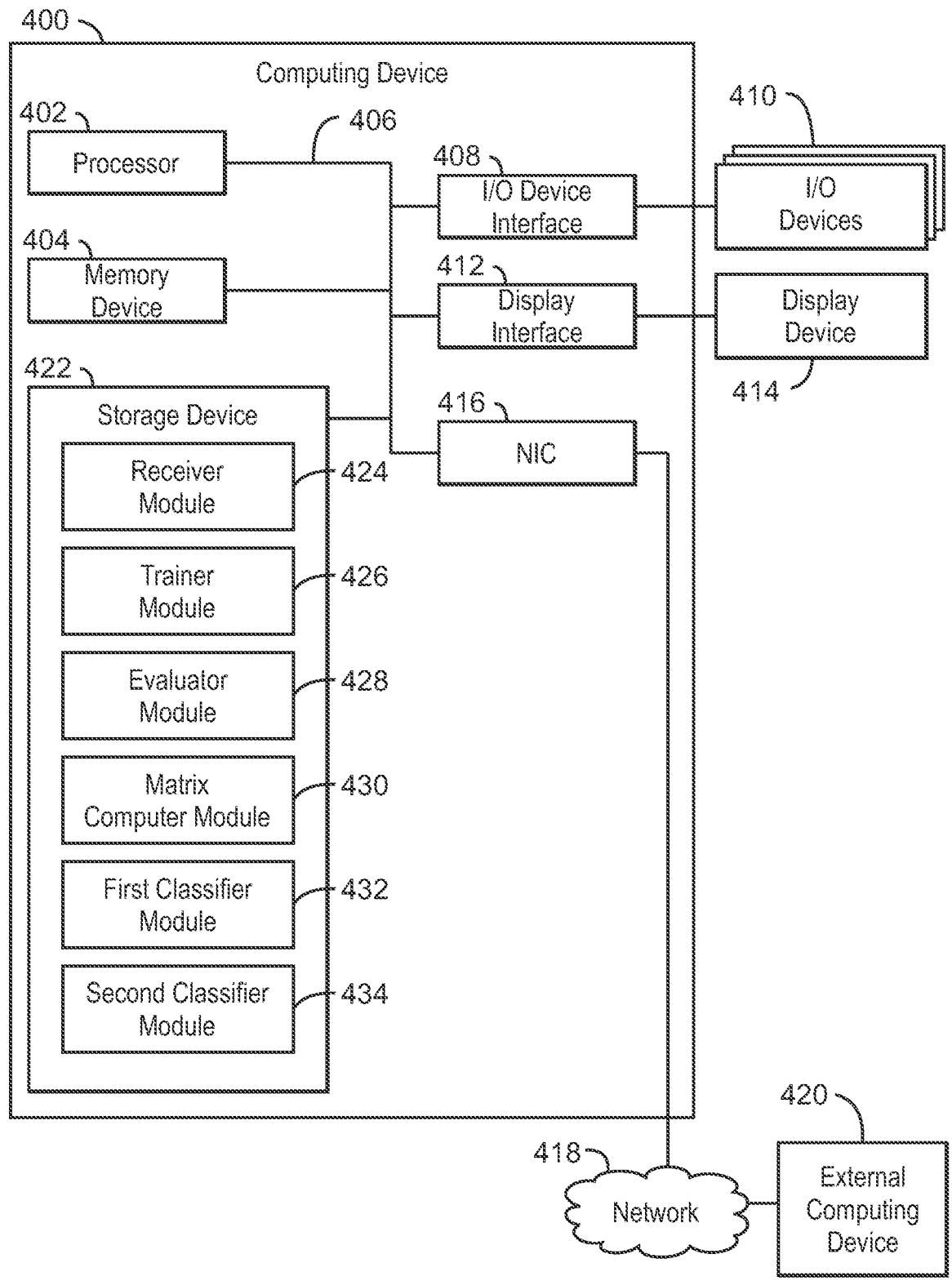
FIG. 4 is a block diagram of an example computing device that can train classifiers to classify data using unlabeled data.

FIG. 4 is block diagram of an example computing device that can train classifiers to classify data using unlabeled data. The computing device 400 may be for example, a server, desktop computer, laptop computer, tablet computer, or smartphone. In some examples, computing device 400 may be a cloud computing node. Computing device 400 may be described in the general context of computer system executable instructions, such as program modules, being executed by a computer system. Generally, program modules may include routines, programs, objects, components, logic, data structures, and so on that perform particular tasks or implement particular abstract data types. Computing device 400 may be practiced in distributed cloud computing environments where tasks are performed by remote processing devices that are linked through a communications network. In a distributed cloud computing environment, program modules may be located in both local and remote computer system storage media including memory storage devices.

The computing device 400 may include a processor 402 that is to execute stored instructions, a memory device 404 to provide temporary memory space for operations of said instructions during operation. The processor can be a single-core processor, multi-core processor, computing cluster, or any number of other configurations. The memory 404 can include random access memory (RAM), read only memory, flash memory, or any other suitable memory systems.

The processor 402 may be connected through a system interconnect 406 (e.g., PCI®, PCI-Express®, etc.) to an input/output (I/O) device interface 408 adapted to connect the computing device 400 to one or more I/O devices 410. The I/O devices 410 may include, for example, a keyboard and a pointing device, wherein the pointing device may include a touchpad or a touchscreen, among others. The I/O devices 410 may be built-in components of the computing device 400, or may be devices that are externally connected to the computing device 400.

The processor 402 may also be linked through the system interconnect 406 to a display interface 412 adapted to connect the computing device 400 to a display device 414. The display device 414 may include a display screen that is a built-in component of the computing device 400. The display device 414 may also include a computer monitor, television, or projector, among others, that is externally connected to the computing device 400. In addition, a network interface controller (NIC) 416 may be adapted to connect the computing device 400 through the system interconnect 406 to the network 418. In some embodiments, the NIC 416 can transmit data using any suitable interface or protocol, such as the internet small computer system interface, among others. The network 418 may be a cellular network, a radio network, a wide area network (WAN), a local area network (LAN), or the Internet, among others. An external computing device 420 may connect to the computing device 400 through the network 418. In some examples, external computing device 420 may be an external webserver 420. In some examples, external computing device 420 may be a cloud computing node.

The processor 402 may also be linked through the system interconnect 406 to a storage device 422 that can include a hard drive, an optical drive, a USB flash drive, an array of drives, or any combinations thereof. In some examples, the storage device may include a receiver module 424, a trainer module 426, an evaluator module 428, a matrix computer module 430, a first classifier module 432, and a second classifier module 434. The receiver module 424 can receive labeled data and unlabeled data. For example, the labeled data may be medical images with labels corresponding to one or more objects, such as various types of tumors found in patients. For example, the medical images may be captured using mammography, computed tomography (CT), magnetic resonance imaging (MRI), X-Ray, etc. The unlabeled data may be images that not include any labels, but may include one or more objects to be annotated. For example, the unlabeled data may be unlabeled images of tumors. The annotated unlabeled data may be used to train a second classifier. The receiver module 424 may also receive data to be classified by the trained second classifier. The trainer module 426 can split the labeled data into a training set and a testing set. The trainer module 426 can train the first classifier module 432 to annotate data based on the training set. For example, the trainer module 426 can train the first classifier module 432 to classify a training set of the labeled data. In some examples, the trainer module 426 can train a second classifier using the annotated data and associated error rates. For example, an embodiment in which the trainer module 426 trains the second classifier using a forward corrected loss has the advantage of noise robustness. In some examples, an embodiment in which the trainer module 426 trains the second classifier using a backward corrected loss has the advantage of being differentiable and being able to be minimized with any suitable back-propagation algorithm. The evaluator module 428 can evaluate the first classifier module 432 using the testing set to generate positive and negative error rates. The matrix module 430 can compute a flipped labels probability matrix based on the associated error rates. For example, the matrix module 430 can generate a flipped labels probability matrix based on the positive and negative error rates for each label. The first classifier module 432 can process a set of unlabeled data to generate annotated data including labels. For example, the first classifier module 432 may be a neural network, such as a convolutional neural network. In some examples, the first classifier module 432 may implemented using decision trees or XGboost, first released Mar. 27, 2014. The first classifier module 432 can process a test set of labeled data to generated labels used to compute associated error rates. The second classifier module 434 can classify a received set of data to be classified. For example, the set of data may include a medical image. The second classifier module 434 may also be a neural network, such as a convolutional neural network.

It is to be understood that the block diagram of FIG. 4 is not intended to indicate that the computing device 400 is to include all of the components shown in FIG. 4. Rather, the computing device 400 can include fewer or additional components not illustrated in FIG. 4 (e.g., additional memory components, embedded controllers, modules, additional network interfaces, etc.). Furthermore, any of the functionalities of the receiver module 424, the trainer module 426, the evaluator module 428, the matrix computer module 430, the first classifier module 432, and the second classifier module 434 may be partially, or entirely, implemented in hardware and/or in the processor 402. For example, the functionality may be implemented with an application specific integrated circuit, logic implemented in an embedded controller, or in logic implemented in the processor 402, among others. In some embodiments, the functionalities of the receiver module 424, the trainer module 426, the evaluator module 428, the matrix computer module 430, the first classifier module 432, and the second classifier module 434 can be implemented with logic, wherein the logic, as referred to herein, can include any suitable hardware (e.g., a processor, among others), software (e.g., an application, among others), firmware, or any suitable combination of hardware, software, and firmware.

Figure 5:
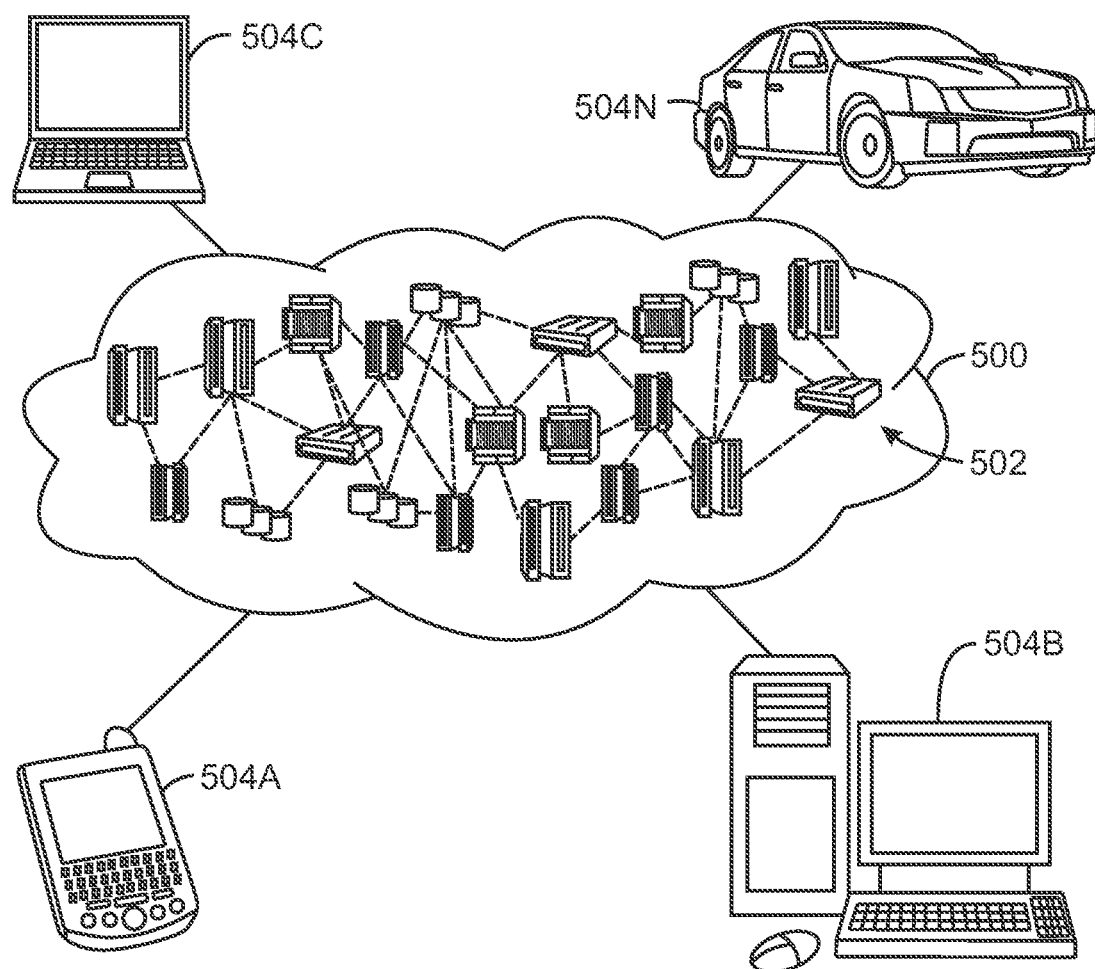
FIG. 5 is a diagram of an example cloud computing environment according to embodiments described herein.

Referring now to FIG. 5, illustrative cloud computing environment 500 is depicted. As shown, cloud computing environment 500 comprises one or more cloud computing nodes 502 with which local computing devices used by cloud consumers, such as, for example, personal digital assistant (PDA) or cellular telephone 504A, desktop computer 504B, laptop computer 504C, and/or automobile computer system 504N may communicate. Nodes 502 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 504A-N shown in FIG. 5 are intended to be illustrative only and that computing nodes 502 and cloud computing environment 500 can communicate with any type of computerized device over any type of network and/or network addressable connection (e.g., using a web browser).

Figure 6:
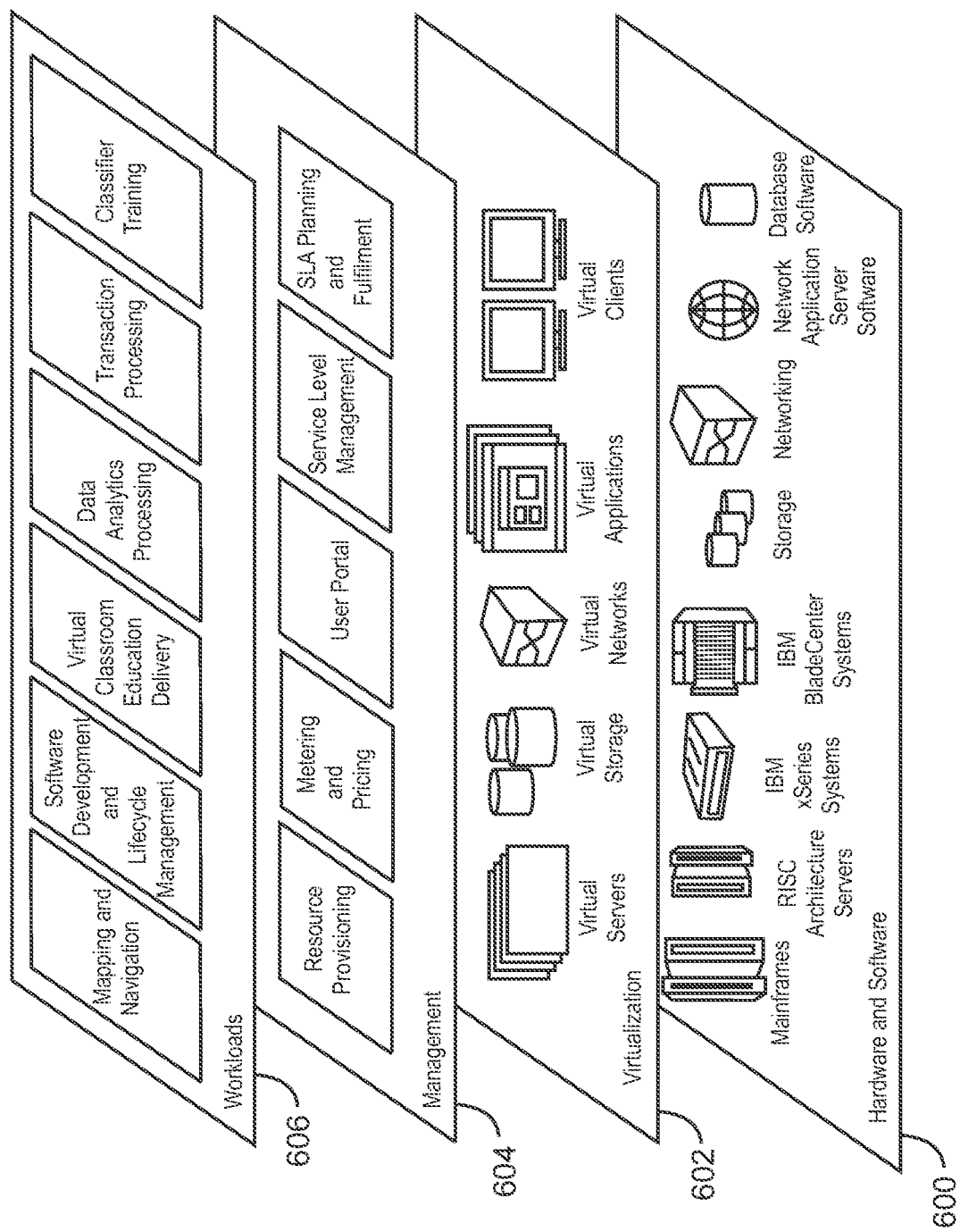
FIG. 6 is a diagram of an example abstraction model layers according to embodiments described herein.

Referring now to FIG. 6, a set of functional abstraction layers provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided.

Hardware and software layer 600 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 602 provides an abstraction layer from which the following examples of virtual entities may be provided: virtual servers; virtual storage; virtual networks, including virtual private networks; virtual applications and operating systems; and virtual clients. In one example, management layer 604 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 606 provides examples of functionality for which the cloud computing environment may be utilized. Examples of workloads and functions which may be provided from this layer include: mapping and navigation; software development and lifecycle management; virtual classroom education delivery; data analytics processing; transaction processing; and classifier training.

The present invention may be a system, a method and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the techniques. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
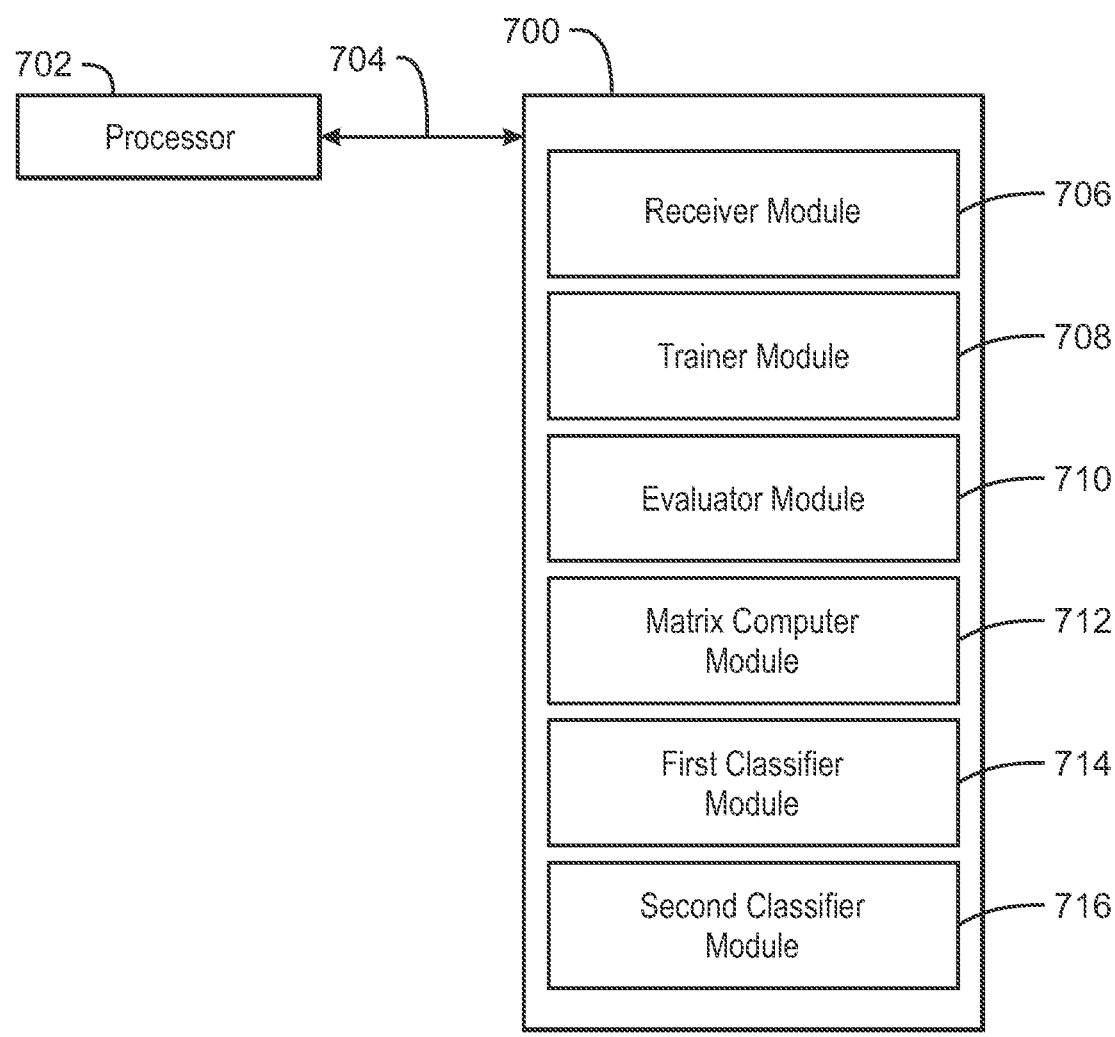
FIG. 7 is an example tangible, non-transitory computer-readable medium that can train classifiers to classify data using unlabeled data.

Referring now to FIG. 7, a block diagram is depicted of an example tangible, non-transitory computer-readable medium 700 that can train classifiers to classify data using unlabeled data. The tangible, non-transitory, computer-readable medium 700 may be accessed by a processor 702 over a computer interconnect 704. Furthermore, the tangible, non-transitory, computer-readable medium 700 may include code to direct the processor 702 to perform the operations of the methods 200A, 200B, and 300 of FIGS. 2A, 2B, and 3.

The various software components discussed herein may be stored on the tangible, non-transitory, computer-readable medium 700, as indicated in FIG. 7. For example, a receiver 706 includes code to receive labeled data. For example, the labeled data may include images annotated with one or more labels. The receiver module 706 also includes code to receive unlabeled data. For example, the unlabeled data may be used to generate annotated data via a first classifier that is used to train a second classifier. The receiver module 706 also includes code to receive data to be classified. For example, the data to be classified may be classified via a second classifier trained on annotated data. A trainer module 708 includes code to split the labeled data into the test set and a training set. The trainer module 708 further includes code to train the first classifier to classify the training set of the labeled data. The trainer module 708 also includes code to train a second classifier using annotated data and the associated error rates. For example, an embodiment in which the trainer module 708 trains the second classifier using a forward corrected loss has the advantage of noise robustness. In some examples, an embodiment in which the trainer module 708 trains the second classifier using a backward corrected loss has the advantage of being differentiable and being able to be minimized with any suitable back-propagation algorithm. An evaluator module 710 includes code to evaluate a trained first classifier on a test set of labeled data to generate error rates for a number of labels. A matrix computer module 712 includes code to compute a flipped labels probability matrix based on the error rates and calculate a loss based on the flipped labels probability matrix. A first classifier module 714 includes code to process a set of unlabeled data to generate annotated data including labels and associated error rates. For example, the first classifier module 714 may be trained by the trainer module 708 based on the training set. A second classifier module 716 includes code to classify unlabeled data. For example, the second classifier module 716 may be trained by the trainer module 708 on annotated data generated by the first classifier module 714 using a loss based on positive and negative error rates computed by the evaluator module 710. Thus, the second classifier module 716 may be trained on unlabeled data that has the advantage of not having to be labeled manually. It is to be understood that any number of additional software components not shown in FIG. 7 may be included within the tangible, non-transitory, computer-readable medium 700, depending on the particular application.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. It is to be understood that any number of additional software components not shown in FIG. 7 may be included within the tangible, non-transitory, computer-readable medium 700, depending on the specific application.

The descriptions of the various embodiments of the present techniques have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising a processor to:
   evaluate a trained first classifier on a test set of labeled data to generate error rates for a plurality of labels;
   process a set of unlabeled data via the trained first classifier to generate annotated data comprising labels and associated error rates; and
   train a second classifier using the annotated data and the associated error rates.

2. The system of claim 1, wherein the processor is to compute a flipped labels probability matrix based on the associated error rates.

3. The system of claim 1, wherein the trained classifier is trained to classify a training set of the labeled data.

4. The system of claim 1, wherein the processor is to train the second classifier using a forward corrected loss.

5. The system of claim 1, wherein the processor is to train the second classifier using a backward corrected loss.

6. A computer-implemented method, comprising:
evaluating, via a processor, a trained first classifier on a test set of labeled data to generate error rates for a plurality of labels;
generating, via the trained first classifier, annotated data comprising labels and associated error rates based on a set of unlabeled data; and
training, via the processor, a second classifier using the annotated data and the associated error rates.

7. The computer-implemented method of claim 6, wherein training the second classifier comprises computing a flipped labels probability matrix based on the error rates and calculating a loss based on the flipped labels probability matrix.

8. The computer-implemented method of claim 6, comprising receiving the labeled data, splitting the labeled data into the test set and a training set, and training the first classifier to classify the training set of the labeled data.

9. The computer-implemented method of claim 6, wherein training the second classifier comprises using a forward corrected loss.

10. The computer-implemented method of claim 6, wherein training the second classifier comprises using a backward corrected loss.

11. A computer program product for annotating training data, the computer program product comprising a computer-readable storage medium having program code embodied therewith, wherein the computer readable storage medium is not a transitory signal per se, the program code executable by a processor to cause the processor to:
evaluate a trained first classifier on a test set of labeled data to generate error rates for a plurality of labels;
process a set of unlabeled data to generate annotated data comprising labels and associated error rates; and
train second classifier using the annotated data and the associated error rates.

12. The computer program product of claim 11, further comprising program code executable by the processor to compute a flipped labels probability matrix based on the error rates and calculate a loss based on the flipped labels probability matrix.

13. The computer program product of claim 11, further comprising program code executable by the processor to receive the labeled data, split the labeled data into the test set and a training set, and train the first classifier to classify the training set of the labeled data.

14. The computer program product of claim 11, further comprising program code executable by the processor to train the second classifier using a forward corrected loss.

15. The computer program product of claim 11, further comprising program code executable by the processor to train the second classifier using a backward corrected loss.

16. A system, comprising a processor to:
receive data to be classified; and
classify the set of data via a classifier trained on annotated data generated from unlabeled data by a second classifier, wherein the classifier is trained using a loss based on error rates generated by the second classifier.

17. The system of claim 16, wherein the loss is based on a flipped labels probability matrix computed based on the error rates.

18. The system of claim 16, wherein the loss comprises a forward corrected loss.

19. The system of claim 16, wherein the loss comprises a backward corrected loss.

20. The system of claim 16, wherein the data comprises a medical image.

21. A computer-implemented method, comprising:
receiving, via a processor, data to be classified; and
classifying, via a classifier trained on annotated data generated from unlabeled data by a second classifier, the set of data, wherein the classifier is trained using a loss based on error rates generated by the second classifier.

22. The computer-implemented method of claim 21, wherein the loss is calculated based on a flipped labels probability matrix generated based on the error rates.

23. The computer-implemented method of claim 21, wherein the loss comprises a forward corrected loss.

24. The computer-implemented method of claim 21, wherein the loss comprises a backward corrected loss.

25. The computer-implemented method of claim 21, wherein data comprises a medical image.

* * * * *